US00PP13303P3

(12) United States Plant Patent
Michalik

(10) Patent No.: US PP13,303 P3
(45) Date of Patent: Dec. 3, 2002

(54) VARIETY OF GERANIUM PLANT NAMED 'FIWOSCARL'

(75) Inventor: Andrea Michalik, Dresden (DE)

(73) Assignee: Elsner Pac Jungpflanzen (DE)

( * ) Notice: Subject to any disclaimer, the term of this patent is extended or adjusted under 35 U.S.C. 154(b) by 63 days.

(21) Appl. No.: 09/733,022

(22) Filed: Dec. 8, 2000

(65) Prior Publication Data

US 2002/0073468 P1 Jun. 13, 2002

(51) Int. Cl.[7] ..... A01H 5/00

(52) U.S. Cl. ..... Plt./330

(58) Field of Search ..... Plt./325, 330

*Primary Examiner*—Kent L. Bell
(74) *Attorney, Agent, or Firm*—Webb Ziesenheim Logsdon Orkin & Hanson, P.C.

(57) ABSTRACT

A new and distinct zonal geranium plant with red colored flowers above medium green foliage. The plant is suitable for pot planting or as a bedding plant.

1 Drawing Sheet

VARIETY DENOMINATION

'Fiwoscarl'.

BACKGROUND OF THE INVENTION

The present invention comprises a new and distinct cultivar of *Pelargonium×hortorum* known by the varietal name 'Fiwoscarl'. The new variety was discovered in 1998 in a selective breeding program in Dresden, Germany. The new variety is the result of combination breeding between 40 stellar-type unnamed, unpatented selections from breeding group 97K-34. Plants of the new geranium differ from the plants of the breeding group in having stronger leaf zonation, shinier flowers, and pointed upper petals. The new variety was frist asexually reproduced by cuttings in Dresden, Germany in 1999. The new variety has been trial and field tested and has been found to retain its distinctive characteristics and remain true to type through successive propagations.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out in Dresden, Germany. The following observations and measurements were taken 6 months after planting rooted cuttings in 19 cm diameter pots. The color readings were taken outdoors in diffuse light during summer. Color references are primarily to The R.H.S. Colour Chart of The Royal Horticultural Society of London.

PLANT

Classification:
- *Botanical.*—*Pelargonium×hortorum.*
- *Commercial.*—Zonal geranium.

Form: Erect.
Height from media surface:
- *Top of foliage.*—45 cm.
- *Top of umbels.*—55 cm.

Width: 40 cm.
Growth: Erect, medium branching.
Strength: Does not require artificial support.
Response time: 3.5 weeks.
Leaves:
- *Width.*—8 cm.
- *Length.*—6 cm.
- *Shape.*—Reniform.
- *Margin.*—Entire; toothed.
- *Texture.*—Smooth.
- *Color.*—Upper surface: Green Group 138A. Lower surface: Green Group 138B. Zone: Greyed-Orange Group 166A.
- *Ribs and veins.*—Color: Green Group 139B.

Petioles:
- *Color.*—Green Group 139B.
- *Length.*—3–5 cm.
- *Diameter.*—2.5 mm.

Stem/branches:
- *Color.*—Green Group 138B.
- *Length.*—35 cm on average.
- *Internode length.*—3–5 cm.

THE BUD

Shape when just showing color:
- *Overall.*—Semi-spherical.
- *Individual bud.*—Narrow, elliptical.

Color: Green Group 143B.
Size when just showing color:
- *Umbel.*—6–8 cm across.
- *Individual bud.*—1–1.5 cm long; 0.5 cm wide.

INFLORESCENCE

Blooming habit: Single.
Size of fully open bloom: 4 cm wide; 6 cm long.
Borne: Umbel; flower on pedicel; pedicel on peduncle.

Flowers:

*Form*.—Zygomorph.

*Average number of infloescences per plant in flowering season*.—40–70.

*Umbel* (*when flowers are open*).—Diameter: 6–8 cm. Depth: 5 cm.

*Number of petals*.—5.

*Size*.—Upper petals: 0.5–0.7 cm wide; 1.5 cm long. Lower petals: 0.6–0.8 cm wide; 1.5 cm long.

*Petals*.—Apex: Strongly pointed. Base: Pointed. Margin: Entire; toothed. Color: Upper surface: Red Group 40A. Lower surface: Red Group 40C.

*Sepals*.—Quantity: Five. Length: 0.7 cm. Width: 2.5 mm. Apex: Pointed. Base: Wide. Margin: Smooth. Color: Upper surface: Green Group 139C. Lower surface: Green Group 139D.

*Texture and appearance*.—Velvety.

Petaloids: Absent.

Pedicel:

*Length*.—2.5–3.0 cm.

*Color*.—Greyed-Red Group 179A.

Peduncle:

*Length*.—10 cm.

*Color*.—Green Group 138B.

Disease/pest resistance: No susceptibility to diseases or pests has been noted to date.

Lasting quality: Long-lasting; 3–4 weeks per umbel.

REPRODUCTIVE ORGANS

Stamens:

*Anthers*.—3 mm long.

*Filaments*.—Length: 0.5 cm maximum. Color: Bright pink.

*Pollen*.—Dark yellow.

Pistils:

*Number*.—One; five parted.

*Length*.—0.3–0.4 cm.

*Stigma*.—Red.

*Style*.—0.8 cm long.

Ovaries:

*Color*.—Greenish.

*Length*.—0.4 cm.

Fruit: Present with 5 seeds; weak fruit production.

GENERAL CHARACTERISTICS

1. Reniform foliage.
2. Erect, compact growth.
3. Single, star-like flowers.
4. Long-lasting.
5. Good arrangeability with other colors.

I claim:

1. A new and distinct variety of zonal geranium plant substantially as shown and described.

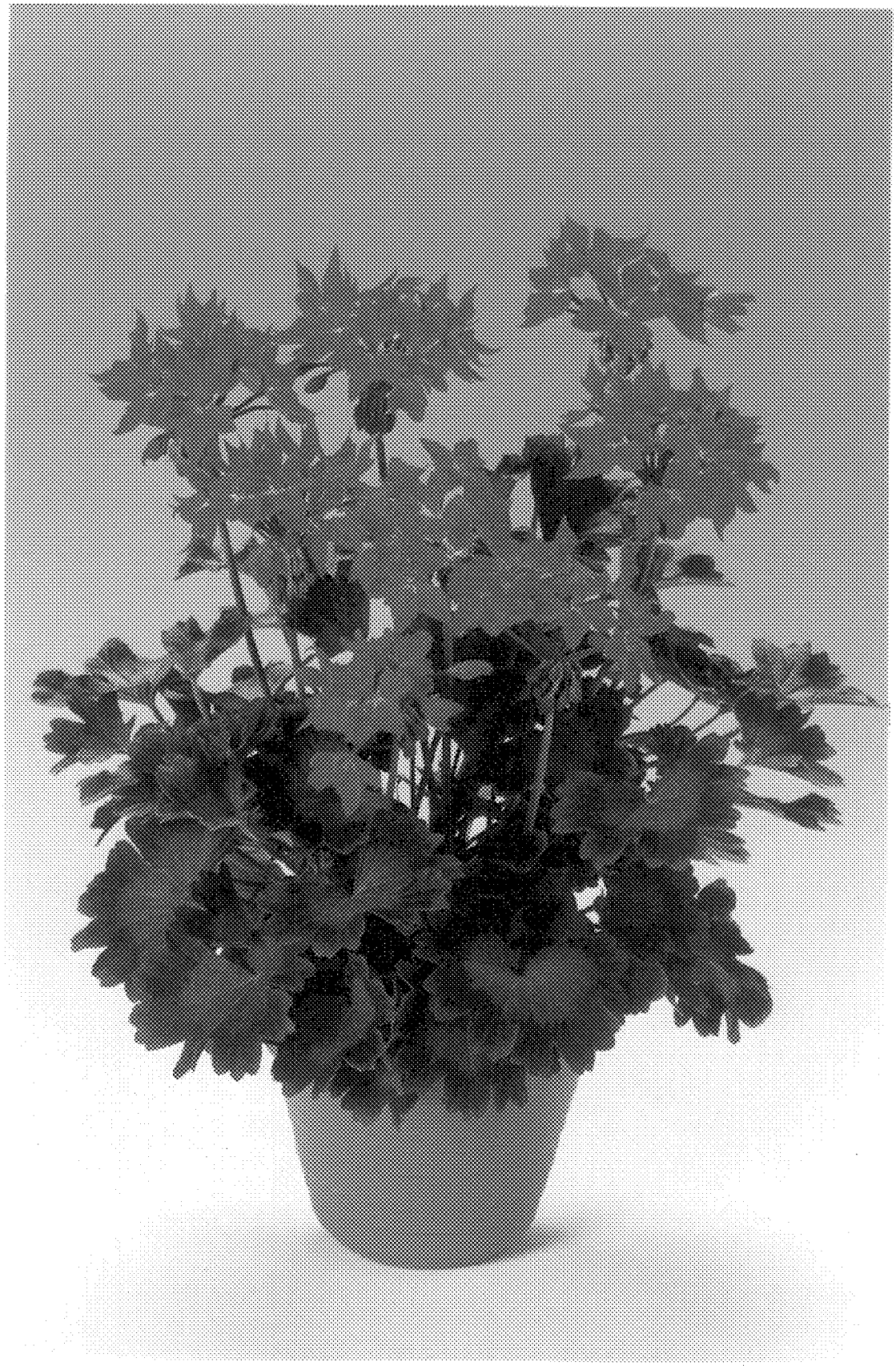

* * * * *